(12) United States Patent  (10) Patent No.: US 8,753,388 B2
Waldock et al.  (45) Date of Patent: Jun. 17, 2014

(54) DELIVERY OF OPHTHALMIC LENSES

(75) Inventors: Terence Arnold Waldock, Meppershall (GB); Stephen Paul Woods, Hertfordshire (GB)

(73) Assignee: Duckworth & Kent Limited, Hertfordshire (GB)

( * ) Notice: Subject to any disclaimer, the term of this patent is extended or adjusted under 35 U.S.C. 154(b) by 1594 days.

(21) Appl. No.: 10/523,179

(22) PCT Filed: Jul. 28, 2003

(86) PCT No.: PCT/GB03/03182
§ 371 (c)(1),
(2), (4) Date: Jan. 5, 2006

(87) PCT Pub. No.: WO2004/010903
PCT Pub. Date: Feb. 5, 2004

(65) Prior Publication Data
US 2006/0155299 A1   Jul. 13, 2006

(30) Foreign Application Priority Data

Jul. 29, 2002 (GB) .................... 0217491.0
Nov. 15, 2002 (GB) .................... 0226677.3

(51) Int. Cl.
*A61F 2/16* (2006.01)
*A61F 9/007* (2006.01)
(52) U.S. Cl.
USPC ........................................ 623/6.12; 606/107

(58) Field of Classification Search
USPC ........................................... 606/107; 623/6.12
See application file for complete search history.

(56) References Cited

U.S. PATENT DOCUMENTS

| | | | | |
|---|---|---|---|---|
| 5,304,182 A * | 4/1994 | Rheinish et al. | ............... | 606/107 |
| 5,702,402 A * | 12/1997 | Brady | ............... | 606/107 |
| 5,772,667 A * | 6/1998 | Blake | ............... | 606/107 |
| 5,944,725 A * | 8/1999 | Cicenas et al. | ............... | 606/107 |
| 6,007,542 A * | 12/1999 | Duprat | ............... | 606/107 |
| 6,497,708 B1 * | 12/2002 | Cumming | ............... | 606/107 |
| 6,503,275 B1 * | 1/2003 | Cumming | ............... | 606/107 |

FOREIGN PATENT DOCUMENTS

WO  WO 99/33411 A1  7/1999

* cited by examiner

*Primary Examiner* — Kathleen Holwerda
*Assistant Examiner* — Sarah W Aleman
(74) *Attorney, Agent, or Firm* — Baker & Hostetler LLP

(57) ABSTRACT

An instrument (110) for rolling a thin ophthalmic lens and inserting the rolled lens into the eye comprises a body (112) in which a plunger (124) is slidable. A thin lens (156) is placed on a lens roller (130) which is slidable transversely of the instrument. The lens is rolled during the sliding movement into a tubular configuration. The rolled lens is then positioned in the instrument in a cylindrical cavity and ready for contact by a push-rod of the plunger (124) so that it is delivered from the instrument through a box in a tip portion (114) of the instrument.

34 Claims, 10 Drawing Sheets

DELIVERY OF OPHTHALMIC LENSES

CROSS-REFERENCE TO RELATED APPLICATIONS:

This claims priority to International Patent Application No: PCT/GB2003/003182, which claims priority to UK Patent Application Nos: 0226677.3, filed Nov. 15, 2002, and 0217491.0 filed Jul. 29, 2002, the entireties of each of which are incorporated by reference herein.

This invention relates generally to the delivery of ophthalmic lenses and instruments for use in the insertion of an intraocular lens into an eye. It is necessary in certain ophthalmic surgical procedures to insert an intraocular lens through a small incision, such as in the phacoemulsification technique of removing cataracts.

In WO-A-99/33411 there is described an instrument for the insertion of an intraocular lens into an eye, which comprises a body portion having a longitudinal axis, a nose portion forward of the body portion and having a lumen through which the lens is arranged to pass, and a plunger movable through the body portion and the nose portion, wherein the nose portion is hingedly connected to the body portion and is movable between an open position in which it is pivoted out of alignment with the longitudinal axis and a closed position in which it is coaxial with the body portion, for the receipt of an intraocular lens therein in the open position.

In the open position the lens can be inserted and then the nose portion is closed and can be locked into place for the operation then of the plunger to dispense the lens from the nose portion.

In use of the aforesaid instrument the lens is folded by the shape of the encircling passageway as the plunger pushes it forwards into the lumen. This is in order to reduce its dimensions so that it can be inserted into a relatively short incision in the eye.

The lenses which have heretofore been available have all had a substantial amount of convexity and therefore thickness in order to be able to achieve the required refractive results. However, thin lenses are now becoming available, which because of the material from which they are made can achieve the required powers of refraction with a greatly reduced lens thickness. Such lenses can have a thickness of as little as 0.4 mm. Hydrophilic acrylic materials are among those which can be used.

There has also been a continuing desire on the part of ophthalmic surgeons to be able to use ever smaller incisions in the eye. However, the incision size has been dictated largely by the dimensions of the folded lens.

It is an object of the present invention to use thin lenses in such a way that they can be inserted into an incision of very small dimensions, for example of as little as 2 mm.

Broadly in accordance with one aspect of the invention there is provided a method of preparing an ophthalmic lens for insertion into the eye which comprises rolling the lens into a tubular configuration. Preferably, the lens is then cooled to maintain its shape for subsequent insertion into the eye.

Also broadly in accordance with the invention there is provided a method of preparing an ophthalmic lens for insertion into the eye which comprises placing the lens on a receiving surface of an injection instrument, and rolling the lens into a tubular configuration in alignment with the longitudinal axis of the instrument for engagement by a plunger.

Preferably, after being rolled the lens is cooled so that it will hold its rolled shape until it has been inserted into the eye, where the warmth of the body will cause it to unroll into its in-use configuration.

Broadly in accordance with the invention there is also provided a device for rolling an ophthalmic lens into a tubular configuration, which comprises a pair of members slidable one relative to the other, one of said members serving to receive and locate the lens, and the movement being arranged to cause rolling of the lens into the tubular configuration.

The present invention is particularly appropriate for use with the instrument described in WO-A-99/33411, which can be thought of as a broken-barrel injector, with the nose pivotable through 90°.

Also in accordance with the present invention in an instrument of the type described in WO-A-99/33411, the forward part of the instrument is provided with a carriage comprising a member slidable relative to the nose of the instrument, said member receiving and locating the lens and the movement being arranged to cause rolling of the lens into a tubular configuration.

The sliding motion is preferably effected transversely of the longitudinal axis of the instrument.

This rolling action is carried out with the nose portion closed. The nose portion is then broken open, for inspection and/or for the lens to be cooled, for example with BSS. The nose portion is then closed again and the rolled lens can be pushed forwards by the plunger through a bore in the lumen.

It has been found in practice that the lens can be rolled so as to have an external diameter of as little as 1.3 mm, which means that the bore in the lumen can have a diameter of about 1.4 mm.

It is also desirable to provide a lens rolling delivery system which avoids the need for alignment pins and for a check pin to maintain the closed engagment.

It is a further object of the present invention to provide a lens rolling delivery system which is easy to manufacture but yet which functions efficiently and reliably.

This may be achieved in accordance with the invention by the use of a carriage comprising a member slidable transversely relative to the nose of the instrument, the member receiving and locating the lens and its movement being arranged to cause rolling of the lens into a tubular configuration, wherein the correct location of the slidable member for delivery of the lens is effected by a click-stop mechanism in combination with resilient biasing means.

The resilient biasing means is preferably a springy arcuate member located on the slidable member and engageable against the nose portion of the instrument, biasing the slidable member in the retractable direction against the force of the click-stop mechanism.

The click-stop mechanism is preferably a flexible strip projecting from the body of the slidable member and engageable behind an abutment provided on the nose portion of the instrument.

The instrument is preferably formed in two parts, a main body portion and a nose portion which are a press fit.

The present invention provides a device for rolling a thin ophthalmic lens into a tubular configuration, comprising a pair of members slidable one relative to the other, one of the members serving to receive and locate the lens and the movement being arranged to cause rolling of the lens into the tubular configuration.

Preferably, each member has a concave recess, the recesses forming at one limit position of the relative sliding movement of the members a cavity which defines the tubular configuration of the rolled lens.

Each recess may be formed upstanding along one edge of a surface of the respective member, one of the said surfaces serving to receive the lens prior to its being rolled by relative sliding movement of the members.

Advantageously, each recess is formed as a step portion between the said surface and further surface extending parallel thereto, the further surface of each member being in sliding contact with the said surface of the other member for sliding movement of one member relative to the other. Preferably, each recess is semi-cylindrical.

Advantageously, at least one of the members is shaped to provide an abutment surface with which a lens being rolled is brought into contact during relative sliding movement of the members, thereby to restrain the lens against rotational movement within the cavity and to promote rolling of the lens.

The abutment surface may be formed by a land which extends along one edge of one of the concave recesses.

Advantageously, the device has stop means defining the limit position, the stop means conveniently comprising a protruding pin on one member which abuts a surface of the other member in the limit position.

The device preferably has means to constrain the members to slide rectilinearly relative to each other, the constraining means conveniently comprising at least one elongate guide element on one member receivable in a corresponding aperture in the other member.

Advantageously, the constraining means comprise a cylindrical pin on one of the members receivable in a cylindrical bore in the other.

Preferably, the constraining means comprise first and second parallel cylindrical pins receivable in respective cylindrical bores.

Conveniently, the pins are both on one member and the bores in the other.

The device advantageously includes means to define the relative position of the two members in which rolling of the lens has been achieved, the means conveniently comprising a click-stop mechanism in combination with resilient biasing means.

The click-stop mechanism may comprise a flexible strip projecting from one of the slidable members and engageable behind an abutment on the other member.

The resilient biasing means may comprise a springy arcuate member located on one of the slidable members and engageable against the other member to bias the slidable members apart.

The arcuate member is preferably located on the respective slidable member adjacent its mid-point and its free ends are engageable against the other member.

An instrument according to the invention for inserting an intraocular lens into an eye may incorporate a device according to the invention and delivering the rolled intraocular lens along an axis with which the lens is aligned in its tubular configuration.

Such an instrument may comprise a body portion, a nose portion forward of the body portion and having a lumen through which the lens is arranged to pass along its said axis, and a plunger movable through the body portion and the nose portion, one of said members constituting the nose portion and the other being slidable relative thereto.

Conveniently, the nose portion is movable relative to the body portion to allow access to a rolled lens located in the lumen of the nose portion.

The nose portion may be hingedly connected to the body portion and is movable between an open position in which said access is allowed and a closed portion in which the plunger is movable into the nose portion.

Alternatively however the nose portion is separable from the body portion and the nose and body portions are a press-fit together, for example by means of at least one pin on one of the portions engaging in a corresponding bore in the other portion.

The invention further provides an instrument for inserting a rolled intraocular lens into an eye, comprising a body portion having a longitudinal axis, a nose portion forward of the body portion and having a lumen through which the lens is arranged to pass, and a plunger movable through the body portion and the nose portion, the nose portion receiving a member which is slidable relative to the nose portion and serves to receive and locate a lens to be inserted, the relative sliding movement of the slidable member and the nose portion being arranged to cause rolling of the lens into a tubular configuration in which the lens is aligned with longitudinal axis and is engaged by the plunger as it moves through the lumen in the nose portion for insertion of the rolled lens into the eye.

In such an instrument, each of the nose portion and the slidable member preferably has a concave recess, the recesses forming at one limit of the relative sliding movement of the nose portion and the slidable member a cavity which defines the tubular configuration of the rolled lens.

Each recess may be formed upstanding along one edge of a surface of the nose portion and the sliding member respectively, one of the said surfaces serving to receive the lens prior to its being rolled by relative sliding movement of the nose portion and the sliding member.

Advantageously, each recess is formed as a step portion between the said surface and a further surface extending parallel thereto, the further surfaces of the nose portion and the sliding member being in sliding contact with the said surfaces of the sliding member and the nose portion, respectively, for sliding movement of the sliding member relative to the nose portion. Preferably, each recess is semi-cylindrical.

Advantageously, at least one of the nose portion and the sliding member is shaped to provide an abutment surface with which a lens being rolled is brought into contact during relative sliding movement of the nose portion and the sliding member, thereby to restrain the lens against rotational movement within the cavity and to promote rolling of the lens.

The abutment surface may be formed by a land which extends along one edge of one of the concave recesses.

Advantageously, the instrument has stop means defining the said limit position, the stop means conveniently comprising a protruding pin on one of the nose portion and the sliding member which abuts a surface of the other of the nose portion and the sliding member in the limit position.

The instrument preferably has means to constrain the sliding member to slide rectilinearly relative to the nose portion, the constraining means conveniently comprising at least one elongate guide element on one of the nose portion and the sliding member receivable in corresponding an aperture in the other of the nose portion and the sliding member.

Advantageously, the constraining means comprise a cylindrical pin on one of the nose portion and the sliding member receivable in a cylindrical bore in the other of the nose portion and the sliding member. Preferably, the constraining means comprise first and second parallel cylindrical pins receivable in respective cylindrical bores.

Conveniently, the pins are both on one of the nose portion and the sliding member and the bores in the other.

The instrument advantageously has means to define the relative position of the nose portion and the slidable member in which rolling of the lens has been achieved, the means conveniently comprising a click-stop mechanism in combination with resilient biasing means.

The click-stop mechanism may comprise a flexible strip projecting from the nose portion or the slidable member and engageable behind an abutment on the sliding member or the nose portion, respectively.

Preferably, the rolling body portion comprises a springy arcuate member located on the nose portion or the slidable member and engageable against the slidable member or the nose portion, respectively, to bias the nose portion and the slidable member apart.

The arcuate member is preferably located on the nose portion or the slidable member adjacent its mid-point and its free ends are engageable against the slidable member or the nose portion, respectively.

The instrument of the invention may be provided in combination with a compression block which is shaped to receive the instrument when the lens-rolling members are in their relative position in which the lens is rolled and ready for delivery.

The invention further provides a method of preparing an ophthalmic lens for insertion into an eye which comprises rolling the lens into a tubular configuration.

The method may include the further stop of cooling the rolled lens prior to insertion so that it tends to maintain its tubular configuration.

Advantageously, the rolled lens has a spiral configuration in transverse section.

Rolling of the lens may be carried out using a separate lens-rolling device according to the invention, from which the rolled lens may be removed, for example by forceps, before insertion into the eye using a further insertion instrument.

Preferably however the lens is rolled and inserted using an instrument according to the invention.

The invention further provides a method of inserting an ophthalmic lens into an eye, preferably a human eye, in which the lens is rolled using a device or an instrument according to the invention, an incision is made in the eye and the rolled lens is inserted, preferably after cooling, through the incision, using an instrument according to the invention or otherwise, and allowed to unroll within the eye.

In order that the invention may be more fully understood, embodiments of the invention will now be described by way of example and with reference to the drawings of this specification, in which.

Figure 26:
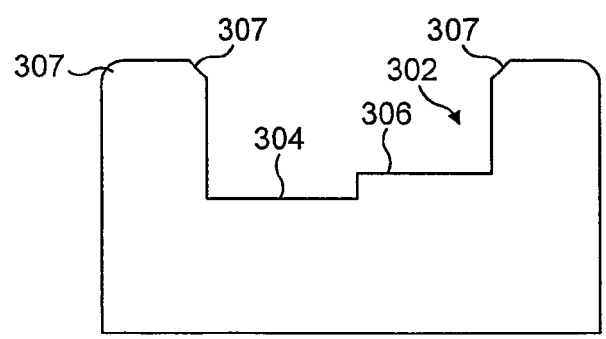
FIG. 26 is a side view of the block of FIG. 25.
Figure 27:
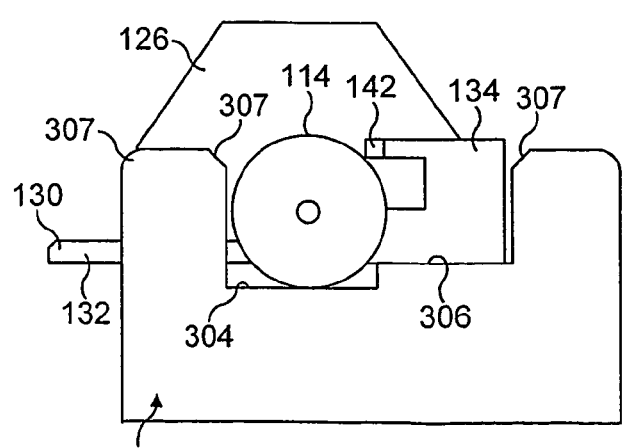

FIG. 27 corresponds to FIG. 26 and shows the block in use.

Figure 1:
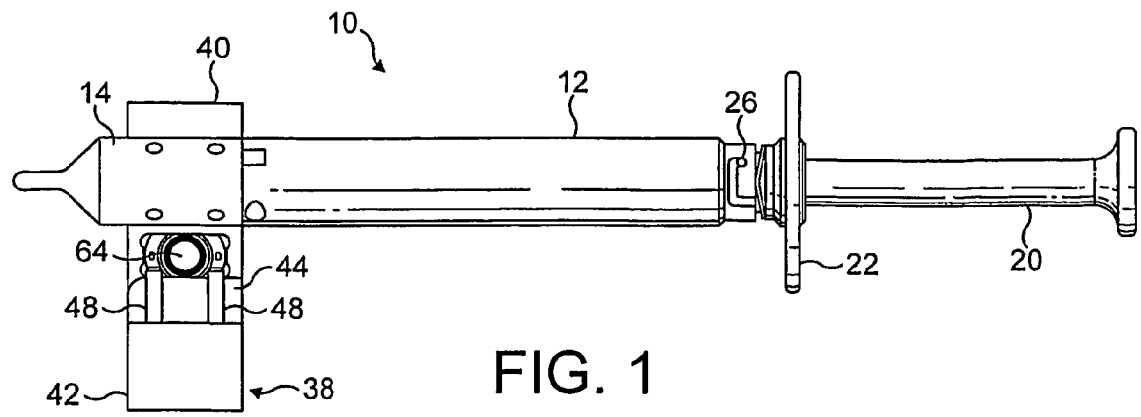
FIG. 1 is a top plan view of an injector instrument having a lens delivery device of the present invention.
Figure 2:
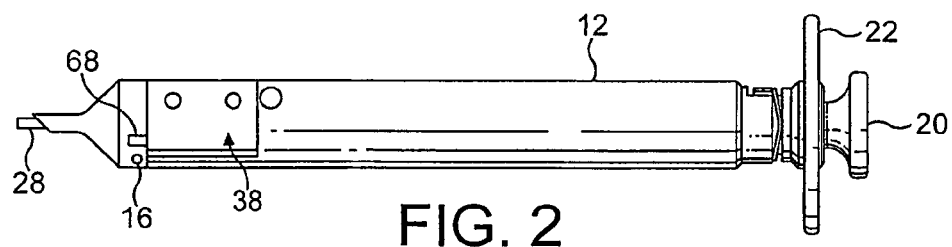
FIG. 2 is a side view of the instrument shown in FIG. 1, but with the plunger fully depressed after insertion of the lens.
Figure 3:
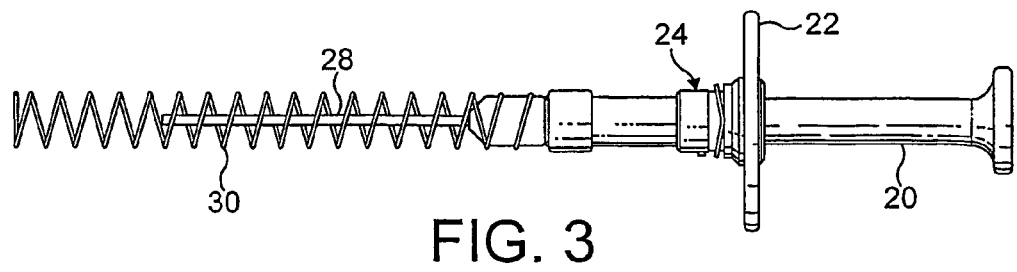
FIG. 3 is a side view of part of the instrument shown in FIG. 1, to illustrate the internal mechanism of the plunger and push rod.

Referring first to FIGS. 1 to 3, there is shown an instrument 10 for the insertion of an intraocular lens into an eye. This instrument functions generally in the manner as described in WO-A-99/33411. The instrument 10 comprises a main body 12, which is shown in more detail in FIG. 9. At the forward end of the body 12 is a nose portion 14 which is pivotable through 90° between a closed position as shown in FIGS. 1 and 2 and an open position (not shown). The pivoting movement takes place about a pivot pin 16 which is housed within a hole 18 (FIG. 9) in the forward end of the main body 12. Projecting rearwardly from the main body of the instrument is a plunger 20. The plunger is arranged to be depressed relative to a flange 22. Forwardly of the flange 22 is a bayonet fitting 24 incorporating a bayonet pin 26 (FIG. 1). This bayonet fitting enables the plunger, and the associated parts shown in FIG. 3 to be withdrawn from the main body 12 of the instrument for cleaning and sterilisation.

As shown in FIG. 3, forwardly of the plunger 20 and connected thereto is a centre rod or push rod 28 which is encircled by a spring 30. The plunger 20 and centre rod 28 are preferably made of polyetheretherketone (PEEK) material, which is particularly appropriate for use with a titanium instrument because of its smooth sliding movement over titanium surfaces. The plunger 20 is thus given a very smooth movement when it is depressed.

Figure 9:
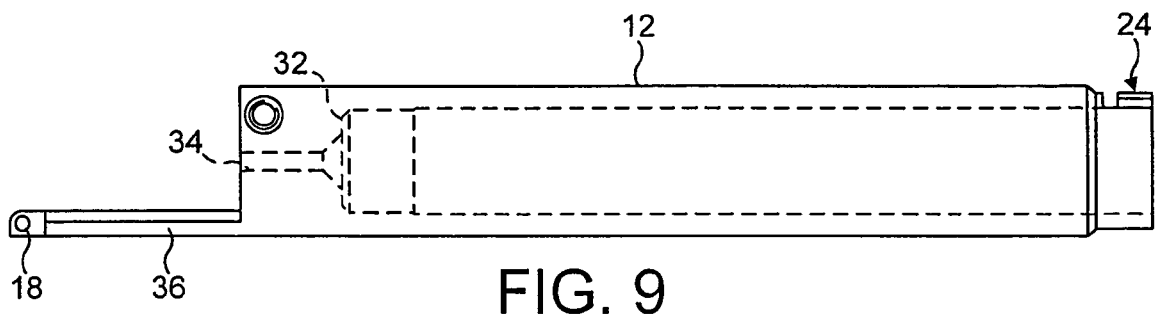
FIG. 9 is a side view of the main body of the instrument shown in FIGS. 1 and 2.

Referring briefly to FIG. 9, there is there shown the main body 12 of the instrument, with a part of the bayonet fitting 24 at its rearward end. The spring 30 is seated at the forward end against an internal surface 32 within the main body and the centre rod 28 is arranged to pass through an internal bore 34 at the forward end of the main body 12. The forward end of the main body terminates in a projecting portion 36 which functions in association with the nose portion and with the lens delivery system which will now be described.

Figure 6:
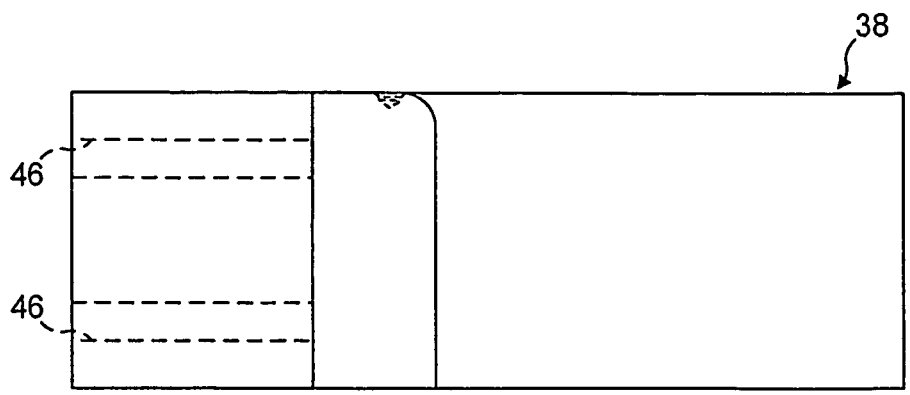
FIG. 6 is a top plan view of the lens roller base of the lens delivery device of the instrument.
Figure 7:
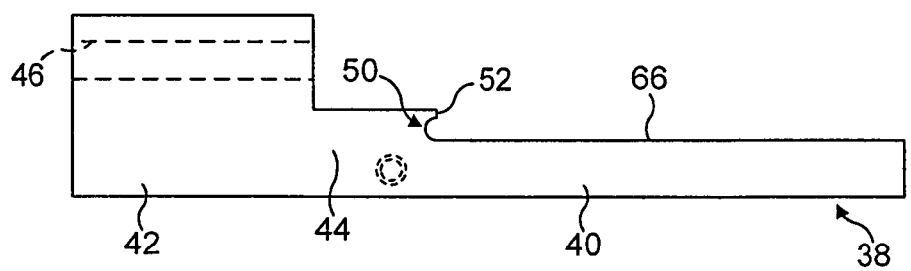
FIG. 7 is a side view of the lens roller base shown in FIG. 6.
Figure 8:
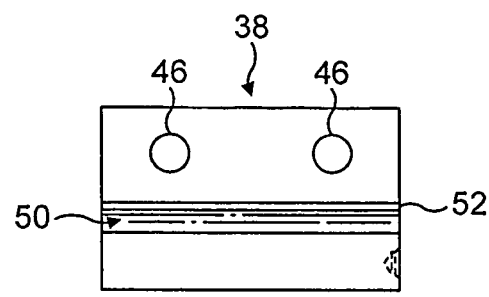
FIG. 8 is the end view of the lens roller base shown in FIGS. 6 and 7.

The lens rolling delivery device will now be described. The delivery device comprises a lens roller base 38, which is shown in use in FIG. 1 and in more detail in FIGS. 6 to 8. The lens roller base 38 is arranged to be slidable transversely to the longitudinal axis of the instrument 10. In FIG. 1, the lens roller base 38 is shown in its position of maximum extension to one side of the instrument. It is arranged to slide linearly across the instrument when the nose portion 14 is closed. The lens roller base 38 comprises a rectangular block of PEEK material, a material chosen to slide smoothly relative to the adjacent surfaces of titanium or titanium alloy. The base 38 comprises a flat, relatively thin front portion 40, with a substantially thicker rear portion 42. Between these two portions is an intermediate stepped portion 44. The thicker rear portion 42 is provided with two bores 46 which receive respective pins 48 (FIG. 1). As shown in FIG. 1, these pins 48, when fitted into the bores 46, project slightly beyond the intermediate stepped portion 44 of the base.

The forward edge of the intermediate stepped portion 44 is shaped to define a concave recess 50 extending across the width of the base 38. This recess can have a diameter of approximately 1.30 mm. At the upper margin of the concave recess 50 is a land or "flat" at the top of the arc, indicated in FIGS. 7 and 8 at 52. The purpose of this "flat" will be described hereinafter.

Figure 4:
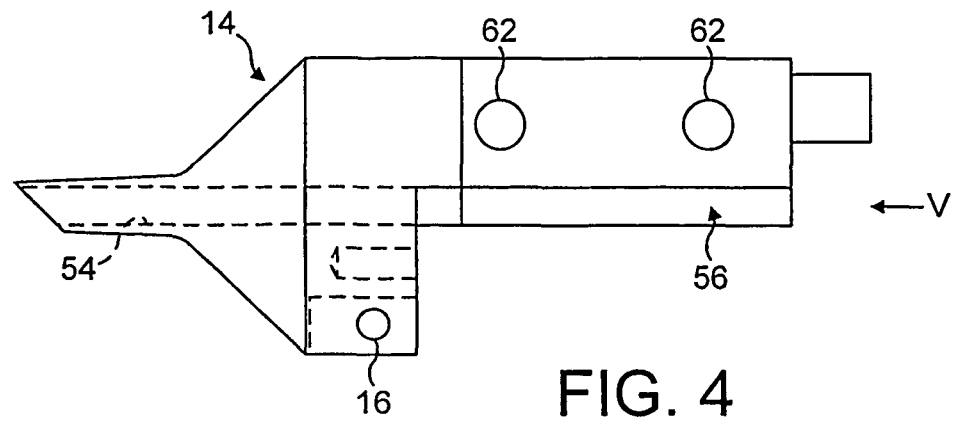
FIG. 4 is a side view of the nose portion of the instrument shown in FIGS. 1 and 2.
Figure 5:
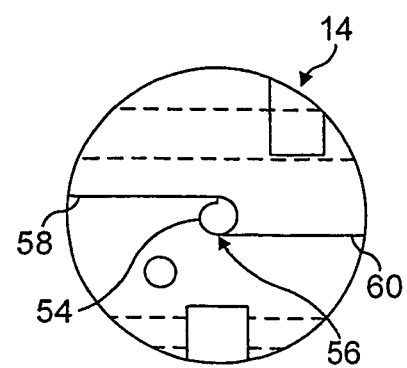
FIG. 5 is the view on arrow V in FIG. 4.

Referring now to FIGS. 4 and 5, these show the nose portion 14 of the instrument. As mentioned above, the nose portion 14 is pivotable through 90° about pivot pin 16. The forward end of the nose portion 14 is shaped as a nozzle with an internal bore 54 through which the lens is pushed towards the incision in the eye. The rearward portion of the nose 14 is shaped to provide a longitudinally extending concave recess 56 between an upper horizontal surface 58 and a lower horizontal surface 60, as shown most clearly in FIG. 5. The diameter of the concave recess 56 is 1.30 mm, i.e. the same as the diameter of the concave recess 50 in the lens roller base 38. The arrangement is such that the two concave recesses 50 and 56 are in alignment facing one another. As will also be appreciated from FIG. 5, the centre of curvature of the concave recess 56 is coincident with the longitudinal axis of the bore 54 and of the injection instrument. The nose 14 is also provided with a pair of bores 62 which are dimensioned and positioned to receive the pins 48 projecting from the lens roller base.

In use, with the plunger 20 retracted as shown in FIG. 1, with the lens roller base 38 slid to the open side as shown also in FIG. 1, and with the nose 14 closed, a thin lens 64 is placed on flat surface 66 of the lens roller base 38 with its periphery within the width of the concave recess 50. A suitable lubricant, for example a balanced salt solution (BSS), may be inserted into the nose portion of the instrument at this stage. With the nose portion 14 still closed, the lens roller base 38 is pushed transversely relative to the longitudinal axis of the instrument so that it slides relative to the nose portion 14. As the lens 64 approaches the concave recess 56 in the nose 14 its periphery will engage the surface of this recess and will begin to roll upwards around the inside of the recess. As the sliding movement continues, and as the two concave recesses approach one another, the leading edge of the lens will strike against the land 52 at the upper margin of the concave recess 50 in the lens roller base and will be brought to a stop. Continuing closure movement will then cause the lens to be rolled up within the cylindrical cavity defined by the two convex recesses 50 and 56 of different radii. It is believed that the different surface properties of the recesses 50 and 56, which are formed in PEEK material and titanium material respectively, may assist in the lens-rolling process.

Figure 10:
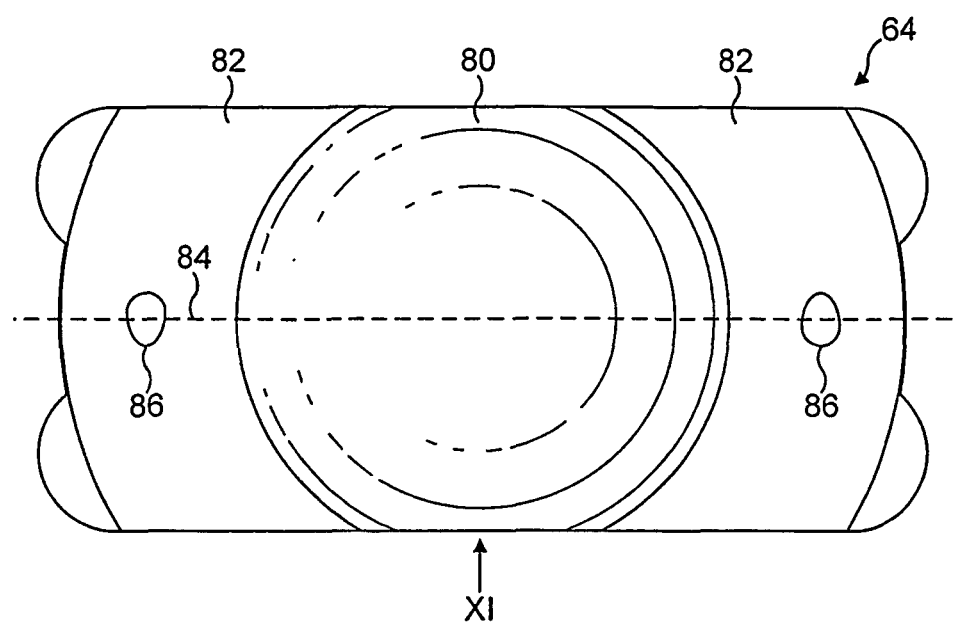
FIG. 10 is a plan view of a thin lens prior to rolling.
Figure 11:
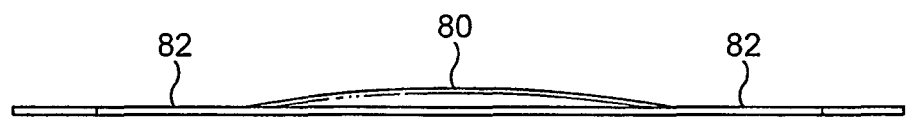
FIG. 11 is a side view of the lens of FIG. 9.
Figure 12:
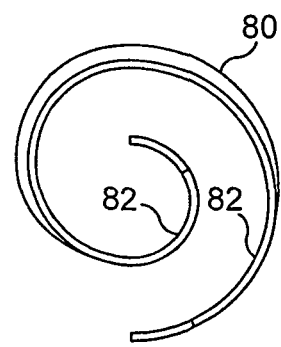
FIG. 12 is an end view in the direction of the arrow XI in FIG. 9 of the lens of FIG. 9 after rolling.

FIGS. 10 to 12 show the rolling process in more detail. The lens 64 is shown in plan in FIG. 9. The lens consists of an optic portion 80, which has a thickness which is dependent on the optical power of the lens, and, to each side, thinner haptic portions 82 which locate the lens in the eye after insertion. The lens 64 measures about 10.5 mm by 5.5 mm and has a maximum thickness of about 0.45 mm. The haptic portions 82 are each about 0.1 mm thick. In this example, the optical power of the lens is determined by the shape of the optic portion 80 which is partially hollow and formed from a series of concentric rings, the number and thickness of which determine the optical power and can be varied accordingly. Pear-shaped openings 86 in the haptic portions provide a visual check that the lens is correctly orientated prior to rolling. FIG. 10 shows the lens in side view. FIG. 11 shows the lens after rolling which takes place about the axis 84 shown in FIG. 9. The rolled lens has a spiral configuration consisting of at least one and typically of two, three or more complete turns. The overall diameter of the rolled lens is about 1.3 mm in this example. Depending upon the thickness of the optic portion 80, there will be a greater or lesser air space between the turns of the spiral or, in parts, no space at all.

When the lens roller base 38 has been advanced to its maximum distance, the projecting pins 48 will be located within the bores 62 in the nose 14. A check stop 68, formed as a pin, then holds the nose 14 and lens roller base 38 in their engaged position. With the two components thus engaged, the nose 14 can be "broken open", i.e. pivoted through 90°, thus opening up the rearward end of the nose and enabling the rolled lens within its cylindrical cavity to be inspected. Desirably, the rolled lens is then also sprayed with a coolant, such as a balanced salt solution (BSS) held at a reduced temperature. This causes the lens to become more rigid and to retain its shape for subsequent delivery through the bore 54 of the nose. After visual inspection and/or cooling of the lens, the nose 14 is pivoted back into its closed position. The lens 64 which is positioned axially within the instrument can then be pushed forwards by depression of the plunger 20. Depression of the plunger 20 causes the leading end of the centre rod 28 to engage the lens and push it forwards through the bore 54 into an incision in the eye. Desirably, one can provide a viscous material between the lens 64 and the leading end of the centre rod 28 in order to provide a more resilient contact. The leading end of the centre rod 28 is flat.

After insertion of the lens 64 the check stop pin 68 is released and the lens roller base 38 can be slid back into its initial, receiving position.

Figure 13:
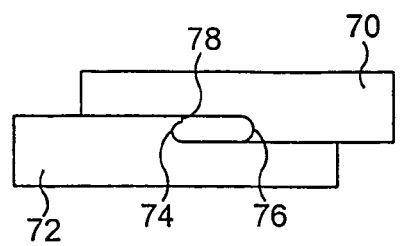
FIG. 13 is a schematic drawing of a separate device for the rolling of a thin lens.

Although the lens rolling delivery device has been described above in relation to its use with an instrument of the type described in WO-A-99/33411, it is to be understood that it is not limited to that particular type of instrument. For example, the lens rolling device could be used with an injection instrument which does not have a pivotable nose but which is designed to be loaded at its forward end with a lens for injection. In this case, a separate lens rolling device can be used, and the lens once rolled can then be loaded into the injection instrument by the use of a suitable transfer device such as forceps. It is therefore within the scope of the present invention to provide a lens rolling device, such as shown for example in FIG. 13, which comprises two members 70, 72 which are formed as blocks slidable relative to one another. The lower block 72 is provided with a concave recess 74 and the upper block 70 is provided with a corresponding concave recess 76. At the top of the arc of concave recess 74 there is provided a land 78 or "flat" which serves as an abutment surface for the rolling lens which is positioned within the cavity defined between the two blocks. Depending upon the structure of the device, one or both of the blocks 70, 72 can be arranged to slide. Once a lens has been positioned between the two blocks and has been rolled by the sliding movement of the blocks, the blocks can be opened in a suitable manner to enable the rolled lens to be removed for transfer to the injection instrument (which may be an instrument according to the invention or otherwise), preferably after cooling to enable the lens to retain its shape.

Figure 14:
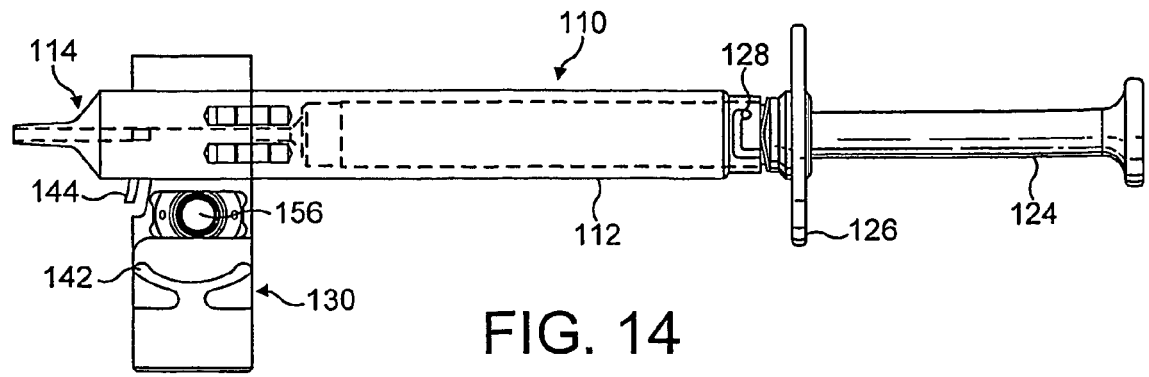
FIG. 14 is a top plan view of another injector instrument embodying a further lens delivery device of the present invention.
Figure 15:
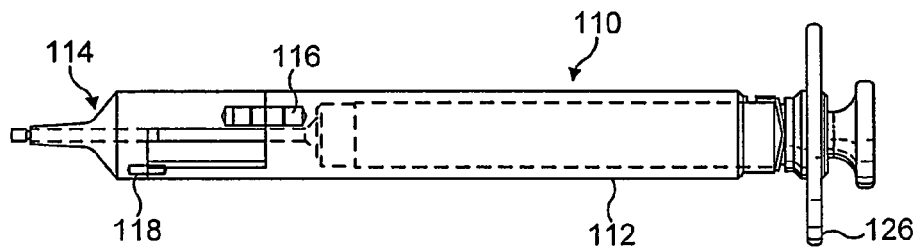
FIG. 15 is a side view of the instrument shown in FIG. 14, but with the plunger fully depressed after insertion of the lens.
Figure 20:
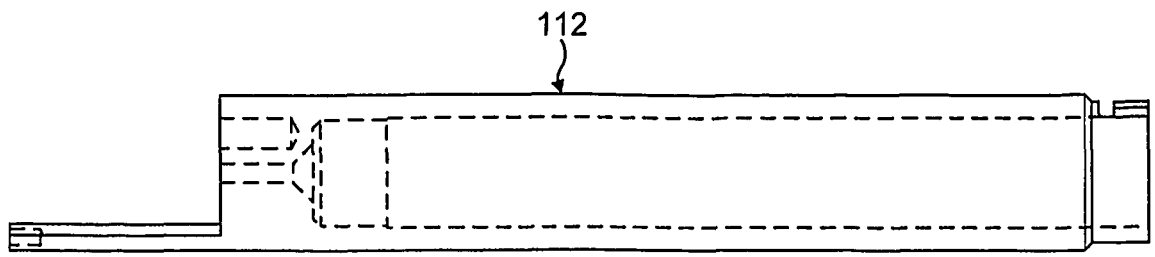
FIG. 20 is a side view of the main body of the injector instrument.
Figure 21:
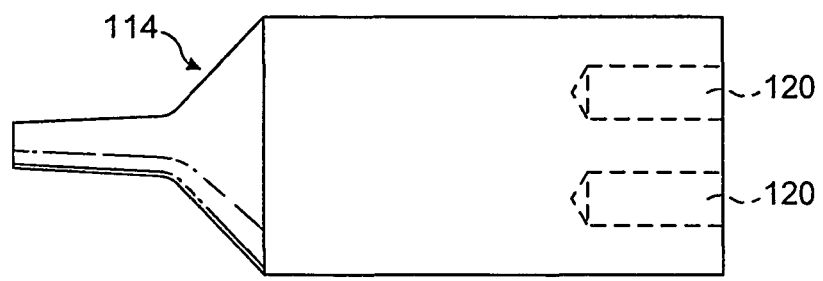
FIG. 21 is a plan view of the nose portion of the instrument.
Figure 22:
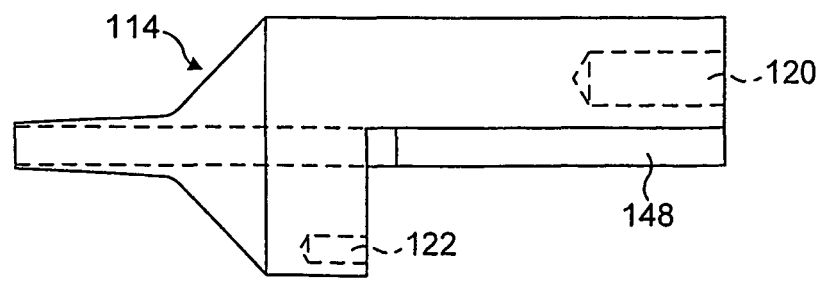
FIG. 22 is a side view of the nose portion shown in FIG. 21.
Figure 23:
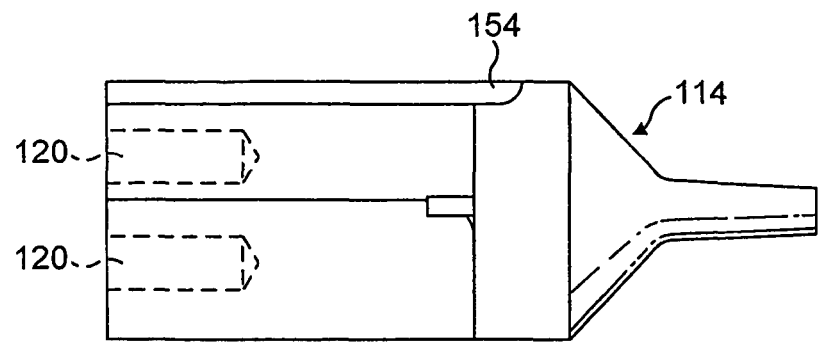
FIG. 23 is the underneath plan view of the nose portion shown in FIGS. 21 and 22.
Figure 24:
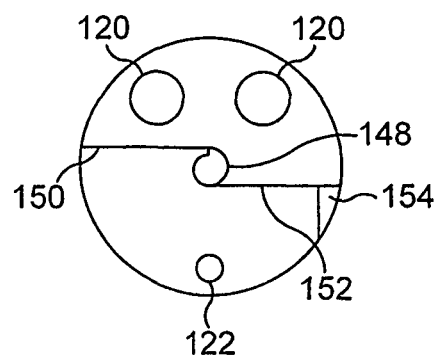
FIG. 24 is an end view of the nose portion shown in FIG. 22, viewed from the right-hand end.

Referring now to FIGS. 14 and 15, these show another complete injector instrument 110 for the insertion of an intraocular lens into an eye. The instrument 110 comprises a body portion 112, which is shown in more detail in FIG. 20. At the forward end of the body portion 112 is a nose portion 114, which is shown in more detail in FIGS. 21 to 24. The main body 112 and the nose portion 114 are a press fit, using a pair of upper pins 116 and a single lower pin 118 to maintain their alignment. The nose portion 114 is provided with a pair of bores 120 to receive the upper pins 116, and with a smaller diameter bore 122 to receive the lower pin 118. Projecting rearwardly from the main body of the instrument is a plunger 124 which is arranged to be depressed relative to a flange 126. Forwardly of the flange 126 is a bayonet fitting 128 which enables the plunger and the associated parts to be withdrawn from the main body of the instrument for cleaning and sterilisation.

Forwardly of the plunger 124, although not shown in the drawings, is a push rod which is encircled by a spring. The forward end of the push rod acts on the lens to deliver it through the nose. The plunger and centre rod are preferably made of polyetheretherketone (PEEK) material, which is particularly appropriate for use with a titanium instrument because of its smooth sliding movement over titanium surfaces.

Figure 16:
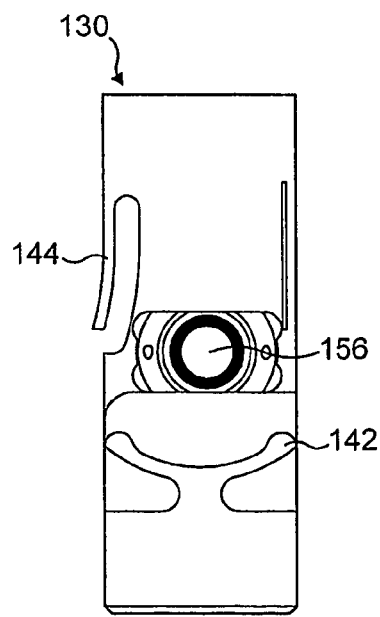
FIG. 16 is a plan view, on an enlarged scale, of the lens roller base.
Figure 17:
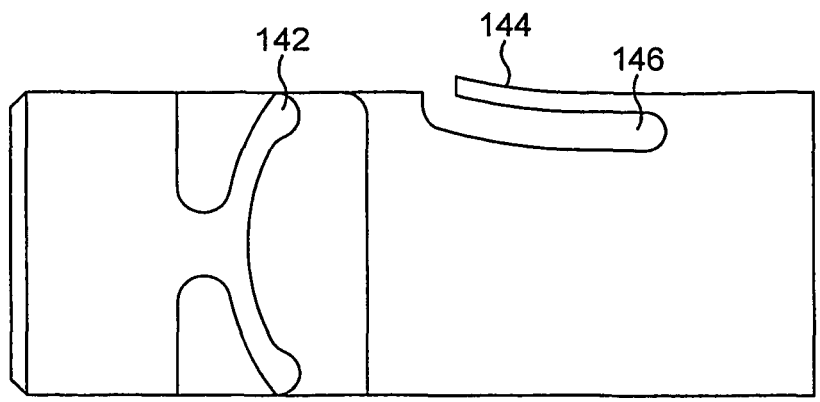
FIG. 17 is a plan view of the lens roller base.
Figure 18:
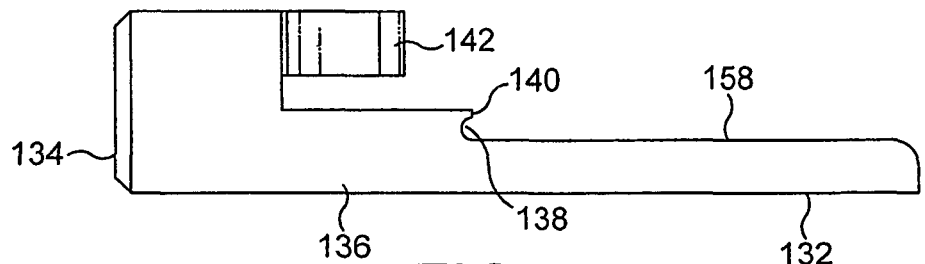
FIG. 18 is a side view of the lens roller base of FIG. 17.
Figure 19:
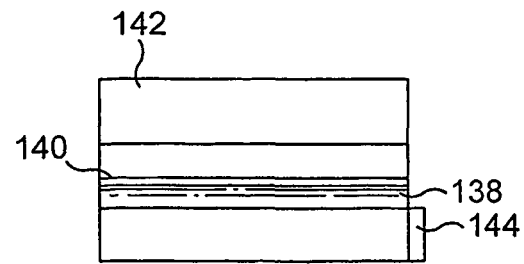
FIG. 19 is the end view of the lens roller base shown in FIGS. 17 and 18.

The lens rolling delivery device will now be described. The delivery system comprises a lens roller base 130, which is shown in use in FIG. 14 and in more detail in FIGS. 16 to 18. The lens roller base 130 is arranged to be slidable transversely to the longitudinal axis of the instrument 110. In FIG. 14, the lens roller base 130 is shown in its position of maximum extension to one side of the instrument. It is arranged to slide linearly across the instrument. The lens roller base 130 comprises a generally rectangular block of PEEK material, a material chosen to slide smoothly relative to the adjacent surfaces of titanium or titanium alloy. The base 130 comprises a flat, relatively thin front portion 132, with a substantially thicker rear portion 134. The thin front portion 132 has an upper flat surface 158. Between the front and rear portions 132,134 is an intermediate stepped portion 136. The forward edge of the intermediate stepped portion 136 is shaped to define a concave recess 138 extending across the width of the base. This recess can have a diameter of approximately 1.30 mm. At the upper margin of the concave recess 138 is a land or "flat" at the top of the arc, indicated in FIGS. 18 and 19 at 140. The thicker end portion 134 of the lens roller base is provided with a forwardly extending arcuate spring portion 142 which, when the lens roller base is pushed through the nose portion of the instrument, is arranged to abut against the side face of the nose portion and by doing so be deformed so as to exert a biasing force in the retraction direction. The two arms of the spring 142 are made sufficiently resilient to enable this effect to be achieved. The thinner portion 132 of the lens roller base is provided with one part of a click-stop mechanism, namely a tongue 144 which has a degree of flexibility and the end of which projects out beyond the side of the base in the form of a tongue. On the inside of the projecting tongue 144 is a closed-end slot 146 in the base material. The tongue 144 can thus be depressed into the slot 146 by pressure exerted on the outside of the end of the tongue.

FIGS. 21 to 24 show details of the nose portion 114 of the instrument. The forward end of the nose portion 114 is shaped as a nozzle with an internal bore through which the lens is pushed towards the incision in the eye. The rearward portion of the nose is shaped to provide a longitudinally extending concave recess 148 between an upper horizontal surface 150 and a lower horizontal surface 152, as shown most clearly in FIG. 24. The diameter of the concave recess 148 is 1.30 mm, i.e. the same as the diameter of the concave recess 138 in the lens roller base 130. The arrangement is such that the two concave recesses 138 and 148 are in alignment facing one another. Also, the centre of curvature of the concave recess 148 is coincident with the longitudinal axis of the bore through the nozzle and of the injection instrument. The nose portion 114 is also provided with a cut-out or recess 154 which is arranged to latch with the tongue 144 of the lens roller base, to function as a click-stop mechanism. The cut-out 154 defines an abutment against which the tongue 144 is engageable.

In use, with the plunger 124 retracted as shown in FIG. 14, and with the lens roller base 130 slid to the open side as shown also in FIG. 14, a thin lens 156 (similar to the lens shown in FIG. 10) is placed on the flat surface 158 of the lens roller base, with its periphery within the concave recess 138. The lens roller base is then pushed transversely relative to the longitudinal axis of the instrument so that it slides across the nose portion 114. As the lens 156 approaches the concave recess 148 in the nose 114 its periphery will engage the surface of this recess and will begin to roll upwards around the inside of the recess. As the sliding movement continues, and as the two concave recesses approach one another, the rolling edge of the lens will strike against the land or flat 140 at the upper margin of the concave recess 138 in the lens roller base and will be brought to a stop. Continuing closure movement will then cause the lens to be rolled up within the cylindrical cavity defined by the two convex recesses. The lens will be rolled into a spiral within this cavity. The rolled lens will then have a diameter of approximately 1.3 mm. The rolling process is as shown in FIGS. 10 to 12.

When the lens roller base 130 has been advanced to its maximum distance, the projecting tongue 144 which has been depressed into the slot 146 during the movement of the lens roller base will reach the cut-out 154 in the nose portion and will latch into this recess 154. At the same time, the arms of the spring member 142 on the lens roller base will have been displaced by engagement against the nose and will be exerting a biasing force in the direction to retract the lens roller base. The combination of this biasing force and the latching of the tongue 144 in the recess 154 serves accurately to locate the lens for delivery by the push rod attached to the plunger.

After delivery of the lens through the incision in the eye, the lens roller base can be released from its delivery position by simply manually depressing the tongue 144 into the slot 146, whereupon the biasing force of the spring member 142 will retract the base sufficiently for it to be withdrawn to the position shown in FIG. 14.

The lens roller base 130 as shown and described is of a shape which is relatively easy to machine from titanium alloy, as compared with the use of alignment pins and bores. The combination of the biasing means and the click-stop mechanism offers a simple solution in terms of ease of manufacture.

Although the invention has been described above in relation to a thin lens which can be rolled to a diameter of about 1.30 mm, the invention is not to be regarded as being limited to any particular dimensions. Similarly, the invention is not be regarded as limited to lenses of any particular material. The invention is applicable to all lenses which are capable of being rolled in the manner described above.

Figure 25:
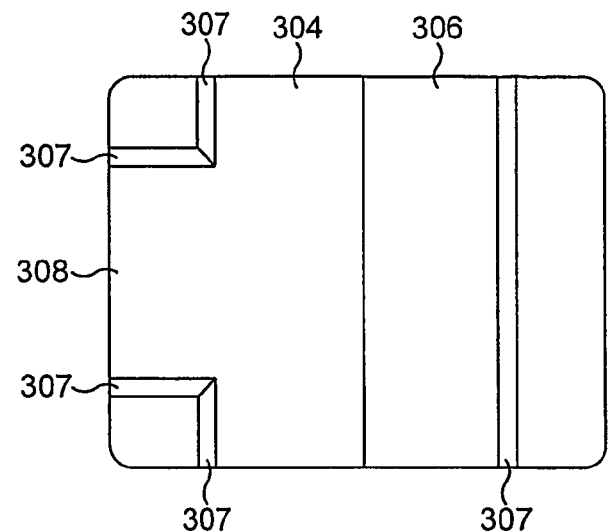
FIG. 25 is a plan view of a compression block for use with the instrument of FIGS. 14 to 24.

FIGS. 25 and 26 of the drawings show a compression block 300 which can be used with the instrument of FIGS. 14 to 24. The block is made from Nylon 66 but any other suitable material, preferably a plastics material, could be used. The block has a basic cuboid shape measuring about 35 mm by 26 mm by 18 mm. A transverse slot 302 of about 20 mm width and rectangular section extends from one side of the block to the other. The slot 302 has deeper and shallower portions 304, 306 of equal width which are of about 10 mm and about 8 mm deep, respectively. The upper edges of the side walls of the slot are bevelled, as indicated at 307.

A lateral slot 308 opens into the deeper transverse slot portion 304. The lateral slot 308 is also of rectangular section and is about 15 mm in width. The sidewalls of the slot are bevelled, again as indicated at 307. The transverse and lateral slots 302,308 thus form together a slot which is T-shaped in plan.

The compression block 300 is used as follows with the instrument of FIGS. 14 to 24. After the lens roller base 130 has been pushed fully into the nose portion against the resilient bias of the spring member 142 and the tongue 144 has latched in the recess 154 but prior to delivery of the lens, the instrument is placed in the compression block 300 such that the nose portion 114 lies in the deeper portion 304 of the transverse slot 302, the thicker portion 134 of the lens roller base 130 lies in the shallower portion 306 of the transverse slot 302 and the thinner portion 132 of the lens roller base 130 lies in the lateral slot 308. In this position, the end surface of the thicker portion 134 and the outer surfaces of the nose portion 114 and the body portion 112 are urged into contact with the side walls of the transverse slot 302 by the biassing force of the spring member 142 which is deformed further as the instrument is inserted into the block, the bevelling 307 of the upper edges of the side walls of the slots 302,308 facilitating this.

FIG. 27 shows the instrument engaged in the compression block as described above. In this position of the roller base 130 relative to the instrument body 112, the lens is rolled to a diameter, in this embodiment about 1.3 mm, such that it can be delivered easily by the plunger 124 through the bore in the nose portion 114. In this embodiment, the diameter of the bore is about 1.4 mm. Whilst the instrument is engaged in the block 300, any tendency for the roller base 130 to creep back away from its fully-inserted position against the bias of the arcuate spring portion 142 is resisted by the compression block. This resistance in turn ensures that no significant unrolling of the rolled lens takes place. Such unrolling is undesirable because it is accompanied by an increase in the diameter of the rolled lens which might lead to a tendency for the lens to stick to the walls of the bore through the nose portion tip 114 as it is delivered by the instrument.

It is desirable that the instrument should be held in the compression block 300 for a period of time of, say, at least 30 s before delivery of the lens takes place. This ensures that the lens assumes its fully rolled configuration. It is also important that the lens be delivered by the instrument promptly after removal from the block 300, in order to ensure that no partial unrolling takes place, or, if not delivered within this time period, is returned to the block.

The instrument is removed from the block in a simple movement by the surgeon prior to delivery, the movement being a simple upward pivoting movement of the instrument about the point of contact of the forward edge of the nose portion 114 and the floor of the deeper groove portion 304.

After delivery of the lens, the tongue 144 is removed from the recess 154 and the roller base 130 withdrawn from the nose portion of the instrument. The instrument can be further dissembled before being cleaned and sterilised prior to further use.

All the instruments described can be used after loading as described by an ophthalmic surgeon to deliver a rolled lens through an incision in the human eye as small as 2 mm in length. The lens is preferably cooled prior to delivery so that it retains its rolled configuration and then unrolls after insertion into the eye.

The invention claimed is:

1. A device for rolling a thin ophthalmic lens into a spiral configuration, the device comprising:
a pair of members that each have a sliding surface that terminates in a respective concave recess, the members being slidable one relative to the other along the respective sliding surfaces such that the concave recesses move relative to each other, the concave recesses forming at one limit position of the relative sliding movement of the members a cavity that defines a central axis and which defines the outward configuration of the rolled lens, and at least one of the members being shaped to provide an abutment surface that is defined by a land that protrudes into the cavity from a wall thereof such that the land defines a first end that contacts the sliding surface of the other member and a second end that is spaced radially inward toward the central axis relative to the first end, and has a length that extends transversely to the direction of relative sliding movement of the pair of members, the abutment surface being configured to contact a lens that is to be rolled at a leading first edge of the lens during relative sliding movement of the members along the surfaces so as to restrain the lens against rotational movement within the cavity and to cause a portion of the lens that comprises an opposed second edge of the lens to curl inwardly of the lens, thereby effecting spiral rolling of the lens.

2. A device according to claim 1, in which each recess is formed upstanding along one edge of the sliding surface of the respective member, one of the said sliding surfaces serving to receive the lens prior to its being rolled by relative sliding movement of the members.

3. A device according to claim 1, in which each recess is formed as a step portion between the said sliding surface and a further surface extending parallel thereto, the further surface of each member being in sliding contact with the said sliding surface of the other member for sliding movement of one member relative to the other.

4. A device according to claim 1, in which each recess is semi-cylindrical.

5. A device according to claim 4, in which the recesses are circularly semi-cylindrical and have respective different radii.

6. A device according to claim 1, wherein the land extends along one edge of one of the concave recesses.

7. A device according to claim 1, further comprising a stop member that defines the limit position.

8. A device according to claim 7, in which the stop member comprises a protruding pin on one member which abuts the surface of the other member in the limit position.

9. A device according to claim 1, having means to constrain the members to slide rectilinearly relative to each other.

10. A device according to claim 9, in which the constraining means comprise at least one elongate guide element on one member receivable in a corresponding aperture in the other member.

11. A device according to claim 10, in which the constraining means comprise a cylindrical pin on one of the members receivable in a cylindrical bore in the other.

12. A device according to claim 11, in which the constraining means comprise first and second parallel cylindrical pins receivable in respective cylindrical bores.

13. A device according to claim 12, in which the pins are both on one member and the bores in the other.

14. A device according to claim 1, having means to define the relative position of the two members in which rolling of the lens has been achieved.

15. A device according to claim 14, in which the means defining the said relative position comprises a click-stop mechanism in combination with a resilient biasing member.

16. A device according to claim 15, in which the click-stop mechanism comprises a flexible strip projecting from one of the members and engageable behind an abutment on the other member.

17. A device according to claim 15, in which the resilient biasing member comprises a springy arcuate member located on one of the members and engageable against the other member to bias the members apart.

18. A device according to claim 17, in which the arcuate member is located on the respective member adjacent its mid-point and its free ends are engageable against the other member.

19. A device for rolling a thin ophthalmic lens into a spiral configuration, the device comprising:
a pair of members that each have a sliding surface that terminates in a respective concave recess, the members being slidable one relative to the other along the respective sliding surfaces such that the concave recesses move relative to each other, the concave recesses forming at one limit position of the relative sliding movement of the members a cavity having a curved interior surface that defines the outward configuration of the rolled lens, and at least one of the members being shaped to provide an abutment surface having an outer end and an inner end such that the curved interior surface extends from the inner end to the outer end when the cavity is formed, the abutment surface defining a length that is transverse to the direction of relative movement such that the abutment surface is configured to contact a lens that is to be rolled at a leading first edge of the lens during relative sliding movement of the members so as to restrain the lens against rotational movement within the cavity and to cause a portion of the lens that comprises an opposed second edge of the lens to curl inwardly of the lens, thereby effecting spiral rolling of the lens.

20. The device of claim 19, wherein the cavity defines a central axis and wherein the outer end contacts the sliding surface of the other member and the inner end is spaced radially inward toward the central axis relative to the outer end.

21. A device according to claim 19, wherein each concave recess is formed upstanding along one edge of the sliding surface of the respective member, one of the said sliding surfaces serving to receive the lens prior to the lens being rolled by relative sliding movement of the members.

22. A device according to claim 19, wherein each recess is formed as a step portion between the said sliding surface and a further surface extending parallel thereto, the further surface of each member being in sliding contact with the said sliding surface of the other member for sliding movement of one member relative to the other.

23. A device according to claim 19, wherein each recess is semi-cylindrical.

24. A device according to claim 19, wherein the abutment surface extends along one edge of one of the concave recesses.

25. A device according to claim 19, further comprising a stop member that defines the limit position.

26. A device according to claim 25, wherein the stop member comprises a protruding pin on one member which abuts the surface of the other member in the limit position.

27. A device according to claim 19, further comprising at least one elongate guide element on one member that is receivable in a corresponding aperture in the other member to thereby constrain the members to slide rectilinearly relative to each other.

28. A device according to claim 19, further comprising a cylindrical pin on one of the members that is receivable in a cylindrical bore in the other member to thereby constrain the members to slide rectilinearly relative to each other.

29. A device according to claim 19 further comprising first and second parallel cylindrical pins receivable in respective cylindrical bores to thereby constrain the members to slide rectilinearly relative to each other.

30. A device according to claim 29, wherein the pins are both on one member and the bores are defined by the other member.

31. A device according to claim 19, further comprising a click-stop mechanism in combination with a resilient biasing member that are configured to define the relative position of the two members in which rolling of the lens has been achieved.

32. A device according to claim 31, wherein the click-stop mechanism comprises a flexible strip that projects from one of the members and is engageable behind an abutment on the other member.

33. A device according to claim 31, wherein the resilient biasing member comprises a springy arcuate member located on one of the members and is engageable against the other member to bias the members apart.

34. A device according to claim 33, wherein the arcuate member is located on the respective member adjacent its mid-point and its free ends are engageable against the other member.

* * * * *